United States Patent [19]

Haase et al.

[11] 4,169,898

[45] Oct. 2, 1979

[54] ANIMAL REPELLANT MIXTURE OF UNDECANONE-2 AND 3-PHENYLPROPENAL

[75] Inventors: Donald A. Haase, Penfield; Frank E. Tamalenus, Fairport, both of N.Y.

[73] Assignee: Mobil Oil Corporation, New York, N.Y.

[21] Appl. No.: 868,601

[22] Filed: Jan. 11, 1978

Related U.S. Application Data

[63] Continuation-in-part of Ser. No. 815,484, Jul. 14, 1977, abandoned.

[51] Int. Cl.² .............................................. A01N 9/24
[52] U.S. Cl. .................................... 424/331; 424/333
[58] Field of Search ............................... 424/331, 333

[56] References Cited

U.S. PATENT DOCUMENTS 3,474,176  10/1969  Freeman .............................. 424/331

OTHER PUBLICATIONS

Lehner et al., "J. Wildl Manage.," 40(1) (1976), pp. 145–150.

*Primary Examiner*—V. D. Turner
*Attorney, Agent, or Firm*—Charles A. Huggett; Ronald J. Cier

[57] ABSTRACT

Mixtures of 3-phenylpropenal with undecanone-2 act in a synergistic manner to provide an animal repellant of improved effectiveness to discourage scavenging animals, in particular, for animals of the dog and cat families.

8 Claims, 1 Drawing Figure

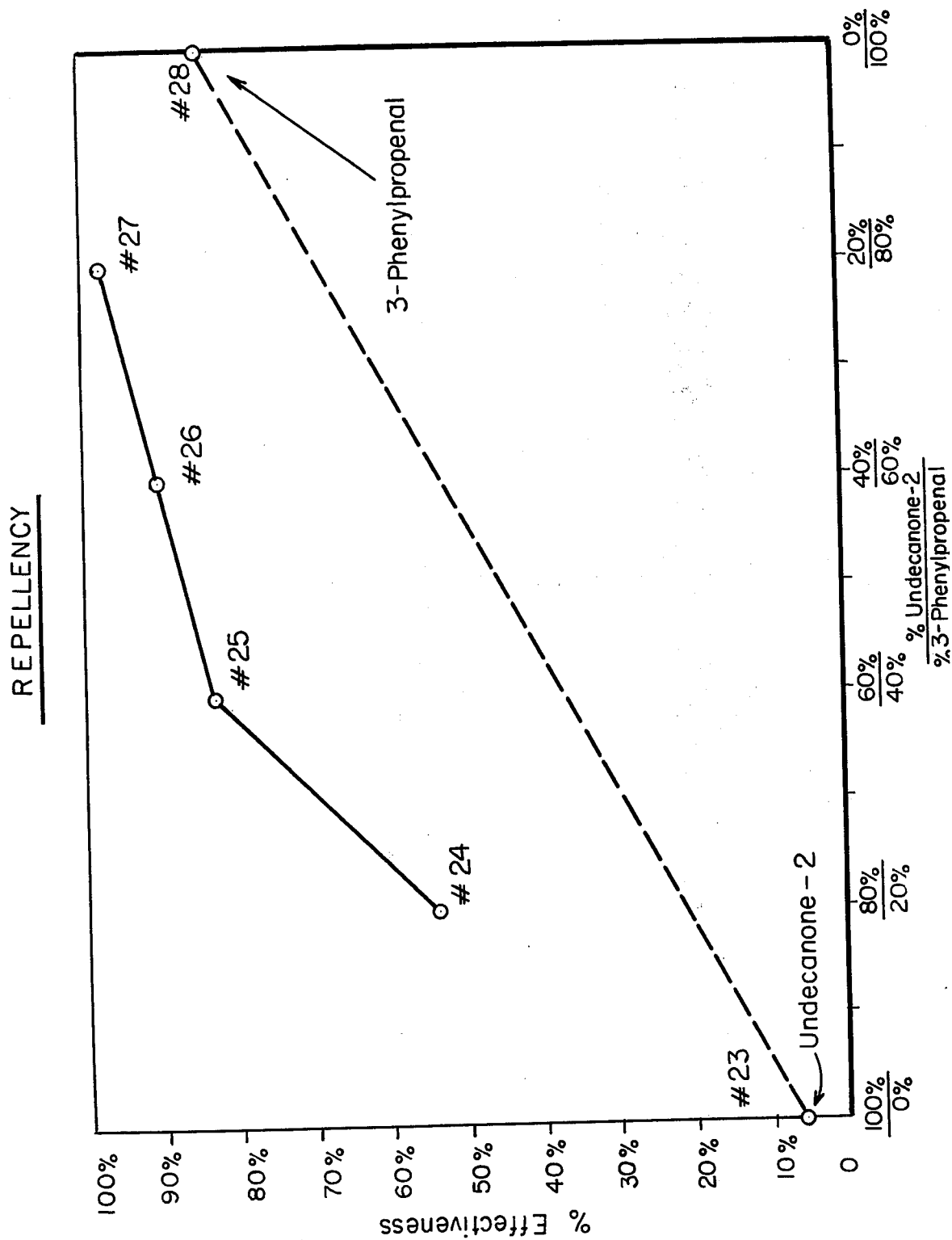

4,169,898

ANIMAL REPELLANT MIXTURE OF UNDECANONE-2 AND 3-PHENYLPROPENAL

CROSS-REFERENCE TO RELATED APPLICATION

This is a continuation-in-part of our copending application Ser. No. 815,484, filed July 14, 1977, now abandoned.

BACKGROUND OF THE INVENTION

1. Field of the Invention

This invention is generally concerned with compositions and methods of controlling animals, and more particularly, it is directed to a novel synergistic mixture of certain compounds for repelling animals and, in particular, dogs and cats.

2. Description of the Prior Art

For reasons of health and convenience it has frequently been found to be desirable to discourage animals from frequenting certain areas. For example, garbage receptacles become both an unpleasant chore to handle and a serious potential health hazard after being ravaged by domestic animals, such as dogs and cats, or by non-domestic animals, such as mice, rats, coyotes, wolves, or the like.

Chemical agents are commonly employed to discourage such animals from approaching those areas from which mankind finds it desirable to exclude them but, while there are many chemical compounds which would effectively repel ravaging animals, there are two restrictions which severely limit the number of chemicals actually available for use. The first restriction is toxicity: the compounds used must be substantially, and preferably completely, non-toxic to mammals since they will frequently be used in proximity to small children and household pets, and the probability of contact and ingestion is high. The second restriction lies with the organoleptic properties of the compound as relates to humans, especially its odor: if the agent is such that it is repulsive or even unpleasant to humans, then it will not be suitable for use in populated areas. Among the relatively few compounds which meet these strictures and are known to have at least some ability to repulse animals are undecanone-2 and 3-phenylpropenal.

Undecanone-2, commonly known as methyl nonyl ketone, is disclosed in U.S. Pat. No. 2,283,471 (Swaine) as being a useful insecticide, and its utility as an animal repellant is taught by Freeman in U.S. Pat. No. 3,474,176 and also by Paulson in Canadian Pat. No. 978,475. The compound has a low level of mammalian toxicity and is one of the active ingredients in many commercial animal repellant formulations.

3-Phenylpropenal (common names: cinnamaldehyde; β-phenylacrolein) is widely used in the perfume industry and is known to exhibit biological activity. U.S. Pat. No. 2,465,854 (Dorman, et al.) teaches the use of both the aldehyde and its derivatives as insecticides. Lehner et al. reported in the Journal of Wildlife Management, 40 (1): 1976 pp 145–150, that the compound showed promise as an olfactory repellant for coyotes and dogs. The fact that this compound is widely used as a synthetic cinnamon flavor and odor additive is testimony to its organoleptic appeal to humans.

SUMMARY OF THE INVENTION

It has now been discovered that mixtures of 3-phenylpropenal with undecanone-2, when used to control the movements of animals, exhibit an unexpected synergistic effect in that the animals find such mixtures to be significantly more repulsive than either of the individual constituents when used individually and in an amount corresponding to the amount of the mixture.

BRIEF DESCRIPTION OF THE DRAWING

The single drawing FIGURE is a graphical representation of Tests #23–28 described hereinafter, illustrating the unexpected synergistic effect of various compositions of our invention.

DESCRIPTION OF THE PREFERRED EMBODIMENTS

The novel animal repellant compositions disclosed herein encompass combinations of 3-phenylpropenal in admixture with synergistically effective amounts of undecanone-2. Such mixtures generally comprise about 10% to about 90% by volume of 3-phenylpropenal and about 90% to about 10% by volume of undecanone-2, the volume percentages of each respective component being taken relative to the other. Particularly preferred are compositions comprising about 40% to about 80% 3-phenylpropenal and about 60% to about 20% undecanone-2.

The compositions of the present invention may be used neat, i.e. without being admixed with a diluent or carrier prior to use, or may be mixed with a suitably inert carrier vehicle prior to application. Such inert vehicle may be any conventional liquid or solid carrier known to those in the art, a few non-limiting examples being: inert animal, vegetable and mineral oils; water; hydrocarbon solvents (e.g. hexane, kerosene, petroleum distillates, benzene, etc.); oxygenated hydrocarbons (alcohols, ketones, and so forth); attapulgite; bentonite; fuller's earth; diatomaceous earth; clay, kaolin; and so forth. The animal repellant composition may be present in the liquid vehicles in the form of a solution or as an emulsion or dispersion. When a solid vehicle is utilized, preferably in the form of a finely divided material such as a dust or powder or the like, the animal repellant compositions disclosed herein are adsorbed or absorbed on such material.

It is contemplated that the compositions of the present invention would be especially useful when applied to containers for discarded edible refuse, as would commonly be present in homes and restaurants. Such containers may be metal or plastic "garbage cans," plastic bags, paper and cardboard boxes, and the like. For the purposes of this disclosure, any conventional container which might be used to hold edible refuse, and thereby be subject to being ravaged by a hungry animal (domestic or otherwise) in search of food, is considered suitable for application of the repellant compositions herein disclosed. Such application may be by hand (e.g. with a brush), by means of a spray applicator of the pump type, or an aerosol-type spray can containing, in addition to the repellant agents and a suitable carrier, a conventional self-propellant composition. It is expected that the application would be directly to the outside of the container itself, but it is foreseeable that such repellant may be beneficially applied to the area immediately surrounding such containers, or mixed with the contents of the containers, or even blended with the structure of the container itself during manufacture (e.g. the so-called disposable plastic garbage bags).

Although the experimental data hereinbelow set forth was obtained utilizing a technique wherein the composition was applied directly to the test subject's food, it is in no way intended that such should be considered the best way to apply the repellant, or is even the most effective way to discourage a hungry animal. Indeed, such conditions are in all likelihood more severe a test of the activity of the composition than would be encountered in a real-life situation and are utilized primarily to establish a controllable basis for comparison of the novel synergistic mixture relative to each of its constituent parts.

It is preferred that the composition of the present invention be used in the form of a solution or an emulsion in an inert liquid carrier at a concentration of about 1% to about 90% by weight of total active ingredient. Especially preferred is 5% to 30% active ingredient in a carrier of corn oil, soybean oil or peanut oil. The preferred method of application is by means of aerosol spray directly to the outside surface of the trash receptacle.

In an effort to establish the superior effectiveness of mixtures of undecanone-2 and 3-phenylpropenal, tests were conducted on each compound alone and on the two in combination. Solutions of each compound alone and the two in combination were prepared, each solution comprising the same amount of total active ingredient in an inert vegetable oil carrier. The test subjects were dogs and cats of mixed background. Each subject was denied food for the 24 hours immediately preceeding the test and the subjects were separated into two groups, a control group and a test group, for each separate test. Each individual test was conducted on a different day and on a different grouping of animals to minimize the influence on the results of any single test subject.

The procedure was to apply the solution to the subject's food and then offer the treated food to the hungry animal and observe the results. The control groups were offered the same food as the test groups, except that it was untreated. The food in all cases was a commercially available meat-based canned pet food, the dogs being offered approximately 7.75 ounces per feeding and the cats approximately 3.5 ounces per feeding.

In all tests the experimental solutions were as follows:

| Repellant A: | 20 cc 3-phenylpropenal |
| --- | --- |
| | 80 cc Corn Oil |
| | 100 cc   Test Solution A |
| Repellant B: | 20 cc undecanone-2 |
| | 80 cc Corn Oil |
| | 100 cc   Test Solution B |
| Repellant C: | 10 cc 3-Phenylpropenal |
| | 10 cc undecanone-2 |
| | 80 cc Corn Oil |
| | 100 cc   Test Solution C |

The solutions of the repellant agents in the inert oil carrier were applied by means of a spray applicator in a dosage of 2.5 cc. of solution to each portion of food, so that each treated portion of food had on it 0.5 cc of the active ingredient. The dish of food was placed in the enclosure with the subject and the animal's behavior observed for 1 hour. If the treated food was not eaten within 1 hour, it was replaced with untreated food.

| Tests No. 1–3 | |
| --- | --- |
| Repellant A: | 20% 3-phenylpropenal |
| Subjects: | Dogs |
| Tests No. 4–6 | |
| Repellant B: | 20% undecanone-2 |
| Subjects: | Dogs |
| Tests No. 7–8 | |
| Repellant C: | 10% 3-phenylpropenal |
| | 10% undecanone-2 |
| Subjects: | Dogs |

TABLE 1
Results of Tests 1–8 on DOGS

| Active Ingredient | Group | No. of Subjects | Ate All Food | Ate Part of Food | Tasted Food | Ate No Food |
| --- | --- | --- | --- | --- | --- | --- |
| 3-Phenylpropenal (20% in corn oil) | | | | | | |
| Test #1 | Control | 10 | 6 | 4 | 0 | 0 |
| Test #2 | Control | 10 | 7 | 2 | 0 | 1 |
| Test #3 | Control | 10 | 9 | 1 | 0 | 0 |
| Total | | 30 | 22 | 7 | 0 | 1 |
| Test #1 | Test | 10 | 1 | 1 | 7 | 1 |
| Test #2 | Test | 10 | 0 | 0 | 7 | 3 |
| Test #3 | Test | 10 | 0 | 2 | 5 | 3 |
| Total | | 30 | 1 | 3 | 19 | 7 |
| Undecanone-2 (20% in corn oil) | | | | | | |
| Test #4 | Control | 10 | 10 | 0 | 0 | 0 |
| Test #5 | Control | 10 | 10 | 0 | 0 | 0 |
| Test #6 | Control | 10 | 10 | 0 | 0 | 0 |
| Total | | 30 | 30 | 0 | 0 | 0 |
| Test #4 | Test | 10 | 3 | 0 | 0 | 7 |
| Test #5 | Test | 10 | 3 | 3 | 0 | 4 |
| Test #6 | Test | 10 | 5 | 3 | 0 | 2 |
| Total | | 30 | 11 | 6 | 0 | 13 |
| 3-Phenylpropenal (10% in corn oil) Undecanone-2 (10% in corn oil) | | | | | | |
| Test #7 | Control | 10 | 9 | 1 | 0 | 0 |
| Test #8 | Control | 10 | 10 | 0 | 0 | 0 |
| Total | | 20 | 19 | 1 | 0 | 0 |
| Test #7 | Test | 10 | 0 | 2 | 0 | 8 |
| Test #8 | Test | 10 | 0 | 1 | 0 | 9 |

TABLE 1-continued

| Results of Tests 1-8 on DOGS | | | | | | |
|---|---|---|---|---|---|---|
| Active Ingredient | Group | No. of Subjects | Ate All Food | Ate Part of Food | Tasted Food | Ate No Food |
| Total | | 20 | 0 | 3 | 0 | 17 |

| Test #9-11 | |
|---|---|
| Repellant A: | 20% 3-phenylpropenal |
| Subjects : | Cats |
| Tests #12-14 | |
| Repellant B: | 20% undecanone-2 |
| Subject : | Cats |
| Tests #15-16 | |
| Repellant C: | 10% 3-phenylpropenal |
|  | 10% undecanone-2 |
| Subjects : | Cats |

TABLE 2

| Results of Tests 9-16 on CATS | | | | | | |
|---|---|---|---|---|---|---|
| Active Ingredient | Group | No. of Subjects | Ate All Food | Ate Part of Food | Tasted Food | Ate No Food |
| 3-Phenylpropenal (20% in corn oil) | | | | | | |
| Test #9 | Control | 7 | 4 | 2 | 0 | 1 |
| Test #10 | Control | 12 | 6 | 4 | 0 | 2 |
| Test #11 | Control | 10 | 1 | 8 | 0 | 1 |
| Total | | 29 | 11 | 14 | 0 | 4 |
| Test #9 | Test | 7 | 0 | 1 | 3 | 3 |
| Test #10 | Test | 11 | 1 | 3 | 2 | 5 |
| Test #11 | Test | 10 | 0 | 0 | 5 | 5 |
| Total | | 28 | 1 | 4 | 10 | 13 |
| Undecanone-2 (20% in corn oil) | | | | | | |
| Test #12 | Control | 10 | 9 | 0 | 0 | 1 |
| Test #13 | Control | 10 | 6 | 3 | 0 | 1 |
| Test #14 | Control | 10 | 4 | 3 | 0 | 3 |
| Total | | 30 | 19 | 6 | 0 | 5 |
| Test #12 | Test | 12 | 2 | 3 | 0 | 7 |
| Test #13 | Test | 10 | 3 | 2 | 0 | 5 |
| Test #14 | Test | 10 | 6 | 3 | 0 | 1 |
| Total | | 32 | 11 | 8 | 0 | 13 |
| 3-Phenylpropenal (10% in corn oil) Undecanone-2 (10% in corn oil) | | | | | | |
| Test #15 | Control | 10 | 6 | 3 | 0 | 1 |
| Test #16 | Control | 10 | 10 | 0 | 0 | 0 |
| Total | | 20 | 16 | 3 | 0 | 1 |
| Test #15 | Test | 10 | 0 | 0 | 1 | 9 |
| Test #16 | Test | 10 | 0 | 0 | 2 | 8 |
| Total | | 20 | 0 | 0 | 3 | 17 |

The results of Tests #1-16 are summarized in TABLE 3. As can be seen from the data, both 3-phenylpropenal and undecanone-2 are shown to be mildly effective animal repellants when used alone, with the 3-phenylpropenal demonstrating somewhat more activity than the undecanone-2. One would normally expect that a 50/50 mixture of these compounds, having the same total amount of active ingredient, would show an effectiveness rating falling somewhere between the two, but certainly no better than that of the more effective of the two components.

Surprisingly, the test subjects found the mixture to be extremely repulsive, even to the point of overcoming the strongly instinctive hunger motivation in most of the subject animals. The effectiveness rating of the mixture in these tests indicates it to be an excellent olfactory repellant, vastly superior to either of its constituent parts alone.

TABLE 3

| Summary of Tests 1-16 | | | | |
|---|---|---|---|---|
| | Ate All Food-% | Ate Substantial Amount of Food-% | Tasted Food-% | Ate No Food-% |
| DOGS | | | | |
| 20% 3-Phenylpropenal on Food | | | | |
| Test Group | 3% | 10% | 63% | 23% |
| Control Group | 73% | 23% | 0% | 3% |
| 20% Undecanone-2 on Food | | | | |
| Test Group | 36% | 20% | 0% | 43% |
| Control Group | 100% | 0% | 0% | 0% |
| 10% 3-Phenylpropenal 10% Undecanone-2 | | | | |

TABLE 3-continued

| | Summary of Tests 1-16 | | | |
|---|---|---|---|---|
| | Ate All Food-% | Ate Substantial Amount of Food-% | Tasted Food-% | Ate No Food-% |
| on Food | | | | |
| Test Group | 0% | 15% | 0% | 85% |
| Control Group | 95% | 5% | 0% | 0% |
| | CATS | | | |
| 20% 3-Phenylpropenal on Food | | | | |
| Test Group | 4% | 14% | 36% | 46% |
| Control Group | 38% | 48% | 0% | 14% |
| 20% Undecanone-2 on Food | | | | |
| Test Group | 29% | 21% | 3% | 47% |
| Control Group | 66% | 19% | 0% | 16% |
| 10% 3-Phenylpropenal 10% Undecanone-2 on Food | | | | |
| Test Group | 0% | 0% | 15% | 85% |
| Control Group | 80% | 15% | 0% | 5% |

TESTS #17-22

Another set of tests was conducted similar to the first set detailed above, with the exception that the animals' behavior was not visually observed. Each dish of food was weighed before offering it to the subject and again approximately one hour later to determine if any of the food was gone. No attempt was made to determine if the missing food had been consumed or whether it had been knocked out of the dish by the subject.

The results of Tests #17-22 are summarized in TABLE 4 and generally confirm those detailed in TABLES 1-3.

ounces of a meat-based canned pet food. The dish of food was weighed and then sprayed with 2.5 cc. of the solution of repellant in corn oil. After approximately 15 minutes the dish of food was removed and weighed again to determine how much, if any, food had been consumed. The animal was thereafter offered an equal amount of untreated food as a control. Most of the subjects consumed the control (untreated) food immediately.

The results of Tests #23-28 are summarized in TABLE 5 and shown graphically in the drawing appended hereto.

TABLE 4

| | | Summary of Tests 17-22 | | | | |
|---|---|---|---|---|---|---|
| Active Ingredient | Group | No. of Subjects | Ate All Food-% | Ate Substantial Amount of Food-% | Tasted Food-% | Ate No Food-% |
| | | DOGS | | | | |
| 20% 3-Phenylpropenal Test #17 | Test | 36 | 6% | 11% | 31% | 53% |
| | Control | 36 | 86% | 14% | 0% | 0% |
| 20% Undecanone-2 Test #18 | Test | 33 | 58% | 12% | 9% | 21% |
| | Control | 33 | 85% | 15% | 0% | 0% |
| 10% 3-Phenylpropenal 10% Undecanone-2 Test #19 | Test | 36 | 3% | 14% | 17% | 67% |
| | Control | 36 | 89% | 11% | 0% | 0% |
| | | CATS | | | | |
| 20% 3-Phenylpropenal Test #20 | Test | 33 | 3% | 0% | 24% | 73% |
| | Control | 33 | 79% | 15% | 6% | 0% |
| 20% Undecanone-2 Test #21 | Test | 33 | 24% | 15% | 3% | 58% |
| | Control | 33 | 79% | 21% | 0% | 0% |
| 10% 3-Phenylpropenal 10% Undecanone-2 Test #22 | Test | 36 | 0% | 3% | 19% | 78% |
| | Control | 36 | 89% | 11% | 0% | 0% |

TESTS #23-28

Tests #23-28 demonstrate the effect of varying the relative proportions of the two active constituents. All test solutions contained a total of 20% of the active ingredient (3-phenylpropenal plus undecanone-2) by volume in corn oil.

As in Tests #1-8, the test subjects were dogs which had not been fed for the previous 24 hours. Each dog was first given a bowl containing approximately 7.75

TABLE 5

| | Summary of Tests #23-28 | | |
|---|---|---|---|
| Test No. | Active Ingredient | No. of Subjects | Total % Effectiveness* |
| 23 | 100% Undecanone-2 | 33 | 6% |
| 24 | 80% Undecanone-2 20% 3-Phenylpropenal | 24 | 54% |
| 25 | 60% Undecanone-2 | | |

TABLE 5-continued

Summary of Tests #23–28

| Test No. | Active Ingredient | No. of Subjects | Total % Effectiveness* |
|---|---|---|---|
| | 40% 3-Phenylpropenal | 29 | 83% |
| 26 | 40% Undecanone-2 / 60% 3-Phenylpropenal | 21 | 90% |
| 27 | 20% Undecanone-2 / 80% 3-Phenylpropenal | 29 | 97% |
| 28 | 100% 3-Phenylpropenal | 37 | 84% |

*Subject ate less than 50 grams of food.

Referring now to the graph, the dashed line connecting the point representing the response to undercanone-2 alone (#23) with the point representing the response to 3-phenylpropenal alone (#28) approximates the various levels of effectiveness which one might expect based on a straight-forward calculation of the relative amounts of each component in mixtures of the two compounds. The actual response resulting from mixtures of the two compounds is, however, unexpectedly and significantly better than one would predict from the model represented by line 23–28, as can be seen from the solid line connecting points #24 thru #27 (i.e. the actual mixtures used in tests #24–#27, respectively). For example, using the model to predict a theoretical response for a mixture of 80% undecanone-2 with 20% 3-phenylpropenal (20% total active ingredient in corn oil), one would expect an effectiveness of approximately 22%. The actual result for such a mixture (Test #24) was an effectiveness of 54%. Similarly, the model would predict an effectiveness rating of approximately 68% for a mixture comprising 20% undecanone-2 and 80% 3-phenylpropenal (20% total active ingredient in corn oil), while the actual response was an unexpected 97% effectiveness (Test #27), thereby clearly illustrating the unexpected synergistic effect of mixing these two components.

The compositions of the present invention are expected to provide similar results when employed to repel a broad range of common animal pests, to include not just domestic dogs and cats (as shown in the formal tests) and related species, but also raccoons, skunks, opossums and other animals known for their scavenging propensities. Informal tests conducted in regard to raccoons demonstrate positive results. Preliminary tests indicate that the mixtures of the present invention are ineffective on rodents in laboratory tests conducted with Norway rats.

We claim as our invention:

1. An animal repellant composition comprising from about 5% to about 30% by weight of an active ingredient and from about 70% to about 95% by weight of an inert carrier therefor; said active ingredient being an olfactory repellant comprising a mixture of 1 part of undecanone-2 with 1 to 4 parts of 3-phenylpropenal.

2. An improved animal repellant composition comprising an olfactory repellant of increased effectiveness, said olfactory repellant comprising a mixture of 1 part of undecanone-2 with 1 to 4 parts of 3-phenylpropenal.

3. An improved composition, as defined in claim 2, further comprising an inert liquid or solid carrier vehicle and wherein said carrier vehicle comprises about 10% to about 99% by weight of the composition.

4. An improved composition, as defined in claim 3, wherein said inert carrier vehicle is an inert animal, vegetable or mineral oil.

5. An improved composition, as defined in claim 4 wherein said inert animal, vegetable or mineral oil comprises 70% to 95% by weight of said composition.

6. A method for repelling animals which comprises exposing said animals to the improved olfactory repellant of claim 1.

7. A method for repelling animals which comprises exposing an animal to the improved olfactory repellant composition of claim 2.

8. A method for repelling cats and dogs which comprises exposing a cat or dog to the improved olfactory repellant composition of claim 2.

* * * * *